United States Patent [19]

Lerch et al.

[11] Patent Number: 5,652,339

[45] Date of Patent: Jul. 29, 1997

[54] METHOD OF PRODUCING RECONSTITUTED LIPOPROTEINS

[75] Inventors: Peter Lerch, Bern; Gerhard Hodler, Worb; Vreni Förtsch, Olten, all of Switzerland

[73] Assignee: Rotkreuzstiftung Zentrallaboratorium, Bern, Switzerland

[21] Appl. No.: 361,132

[22] Filed: Dec. 21, 1994

[30] Foreign Application Priority Data

Dec. 31, 1993 [EP] European Pat. Off. .............. 93810920

[51] Int. Cl.$^6$ .............................. C07K 1/00; C07K 14/00
[52] U.S. Cl. ................................................................ 530/359
[58] Field of Search .................................................. 530/359

[56] References Cited

U.S. PATENT DOCUMENTS

| | | | |
|---|---|---|---|
| 4,868,158 | 9/1989 | Masquelier et al. | 514/21 |
| 5,089,602 | 2/1992 | Isliker et al. | 530/359 |
| 5,128,318 | 7/1992 | Levine et al. | 514/2 |

FOREIGN PATENT DOCUMENTS

| | | | |
|---|---|---|---|
| 277849A1 | 8/1988 | European Pat. Off. | A61K 47/00 |
| 329605A1 | 8/1989 | European Pat. Off. | A61K 37/02 |
| WO88/09345 | 12/1988 | WIPO | C07K 15/16 |
| WO93/25581 | 12/1993 | WIPO | C07K 15/00 |

OTHER PUBLICATIONS

Hubsch et al., "A Reconstituted, Apolipoprotein A-1 Containing Lipoprotein Reduces Tumor Necrosis Factor Release and Attenuates Shock in Endotoxemic Rabbits," *Circulatory Shock* 40: 14–23, 1993.

Jonas, A., "Reconstitution of High–Density Lipoproteins," *Methods in Enzymology* 128: 553–582, 1986.

Kistler and Nitschmann, "Large Scale Production of Human Plasma Fractions," *Vox Sang* 7: 414–424, 1962.

Nichols et al., "Nondenaturing Polyacrylamide Gradient Gel Electrophoresis," *Methods in Enzymology* 128: 417–431, 1986.

Quezado et al., "Therapeutic Trial of Reconstituted Human High–Density Lipoprotein in a Canine Model of Gram–Negative Septic Shock," *Journal of Pharmacology and Experimental Therapeutics* 272(2): 604–611, 1995.

Rudel et al., "Separation and Analysis of Lipoproteins by Gel Filtration," *Methods in Enzymology* 129: 45–57, 1986.

Bonomo et al: J. Lipid Res., vol. 29, pp. 380384, 1988.

Matz et al: J. Biol. Chem., vol. 257, pp. 4535–4540, 1982.

Walsh et al: Biochemistry, vol. 22, pp. 3170–3178, 1983.

Chem. Abs.: vol. 119, 173810t, 1993.

*Primary Examiner*—Ponnathapura Achutamurthy
*Attorney, Agent, or Firm*—Seed and Berry LLP

[57] ABSTRACT

Reconstituted high density lipoproteins (rHDL) are produced from apolipoproteins and lipids in that an aqueous apolipoprotein solution with a concentration of 1–40 g protein/l is mixed with an aqueous lipid-detergent solution without mandatory addition of organic solvents, the molar ratio of lipid to detergent being 1:0.5 to 1:4 and the weight ratio of lipid to detergent being 1:1.5 to 1:5, the resultant apolipoprotein-lipid-detergent mixture then being incubated at a temperature in the range of the phase change temperature of the lipid in water ±10° C., and the detergent being at least partially removed.

The rHDL are useful for various prophylactic and therapeutic treatments of diseases that have a connection with lipids and lipidoidal substances. This method is especially suitable for technical and industrial production.

20 Claims, 1 Drawing Sheet

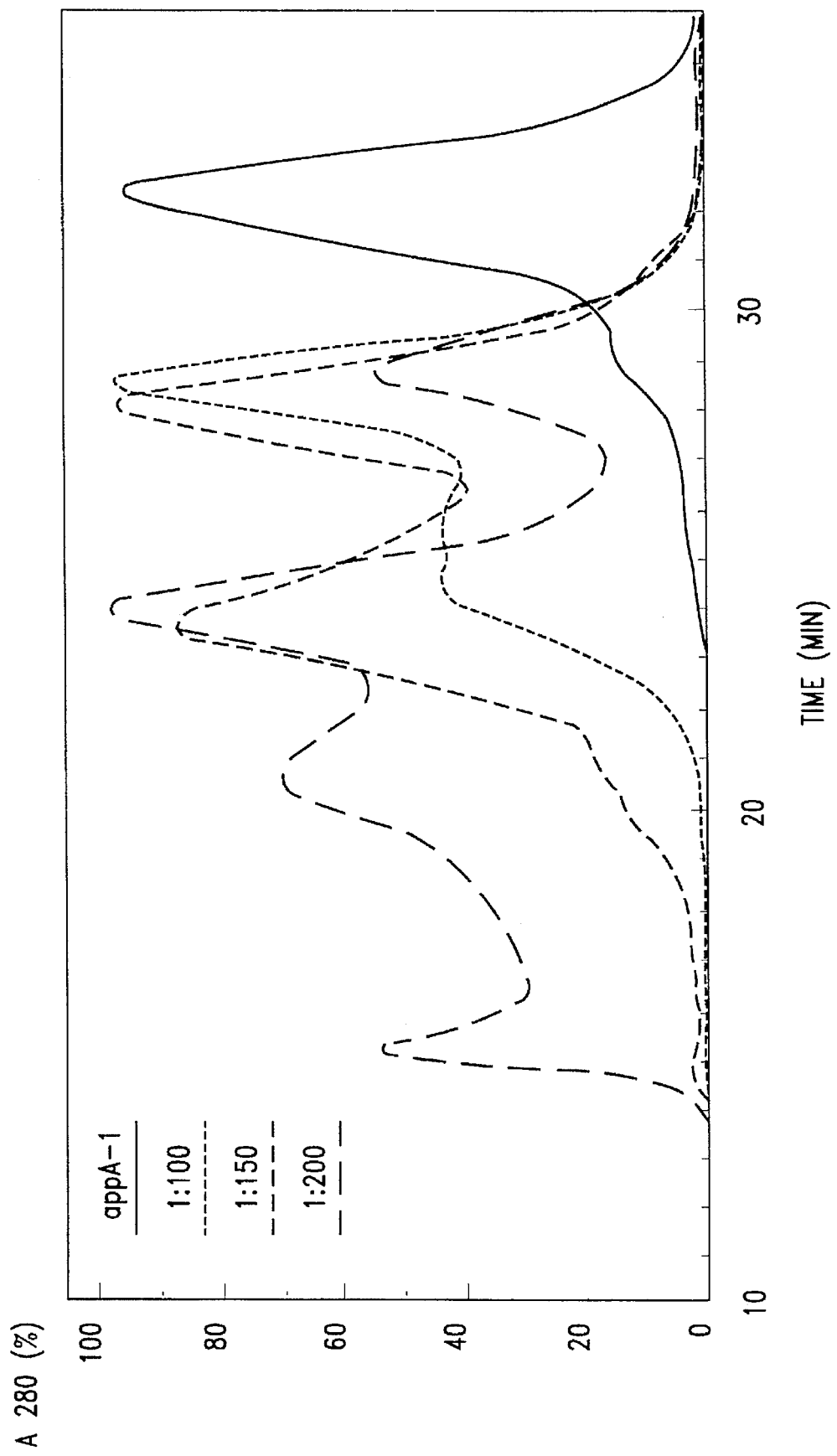

METHOD OF PRODUCING RECONSTITUTED LIPOPROTEINS

TECHNICAL FIELD

This invention concerns a method of producing, in an industrial scale, reconstituted high density lipoproteins (rHDL) from apolipoproteins and lipids. rHDL have the property that they bind lipids and lipoidal substances in the organism, can transport them and can influence their activity. rHDL are thus useful for various prophylactic and therapeutic treatments of disease which have a connection to lipids and lipoidal substances.

BACKGROUND OF THE INVENTION

The lipoproteins of human blood can perform a series of various functions. A well studied and well known function of lipoproteins is the transport of lipids. Lipoproteins have the ability to bind insoluble lipids, to transport them in an aqueous milieu, and bring them to their destination. For some time the individual classes of lipoproteins have been studied more closely in connection with disturbances of lipid metabolism. In the majority of Western countries a positive correlation between cardiovascular diseases and high plasma cholesterol or high low density lipoprotein cholesterol (LDL cholesterol), and a negative correlation to high HDL or high HDL cholesterol was shown by epidemiological studies. Although a whole range of medicines is available on the market which have been shown to have a lipid-lowering effect, it is conceivable that in certain cases a substitution of suitable lipoproteins is advisable. Suitable in such cases are, first of all, the "good" lipoproteins such as HDL or HDL-like particles, such as reconstituted HDL (rHDL) from isolated apolipoproteins and suitable lipids.

Besides the lipids, which are ingested from food, lipoproteins from other lipids or lipoidal substances can be transported or bound. For example, components of dead cells can be bound to lipoproteins and can be given a new function. Lipoidal substances can also be bound to lipoproteins, such as, for example, lipopolysaccharide (LPS). Lipopolysaccharides or endotoxins are components of membranes of gram-negative bacteria. If sufficiently large quantities of endotoxin are able to enter the cardiovascular system, this can lead to septic shock or even death. As a result of binding of LPS to lipoproteins, the function or activity of LPS can be modulated. The activity of LPS can be considerably changed in vivo or in vitro through addition of lipoproteins or lipoprotein-like particles. Thus it could be shown in vivo that the addition of reconstituted HDL inhibited the formation of tumor necrosis factor (TNF), an important mediator of sepsis. In vivo, the symptoms of shock could be greatly reduced through the administration of HDL or rHDL.

Besides interactions of lipoproteins or reconstituted lipoproteins with lipids or lipoidal substances, Interactions of lipoproteins with proteins have also been described:

lipoproteins can enter into interactions with individual components of the complement system, and can therefore influence their activity;

components of the coagulation systems are likewise known which are to be found in the lipoprotein fraction, that is, which are associated with certain lipoproteins;

acute phase proteins such as serum amyloid A (SAA) are found in the HDL fraction;

and furthermore the adsorption of certain proteins on surfaces can be influenced by pretreatment with lipoproteins.

Through specific or non-specific binding to cells, lipoproteins can also influence cellular activity:

The platelets' ability to be activated can be reduced through binding of HDL or can be stimulated by addition of LDL;

Monocytes and macrophages likewise have receptors for lipoproteins; the binding or uptake of lipoproteins can lead to changes in the activities of these cells;

The activity of other cells involved in the host defense system such as neutrophils can likewise be modified or modulated through binding of lipoproteins;

Furthermore, the growth of tumor cells, shown using glyoblastoma cells as an example, can also be influenced through lipoproteins.

In scientific literature reports are to be found moreover which describe interactions of lipoproteins with pathogens; for example, an antimicrobial activity is ascribed to lipoproteins. It has been shown that viruses can also be inactivated by means of lipoproteins, or, using trypanosomes as an example, parasites can be influenced or respectively inhibited.

These examples show diverse possibilities for the use of lipoproteins or rHDL in prophylactic and therapeutic applications.

Lipoproteins are divided into four main classes:

chylomicrons, which are particles that consist predominantly of triglycerides and which normally appear in larger quantities in plasma only after fatty meals, VLDL (Very Low Density Lipoproteins), LDL (Low Density Lipoproteins), and HDL (High Density Proteins). The nomenclature arises from the isolation of lipoproteins by means of ultracentrifugation. Classically, the lipoproteins are isolated in a density gradient. This method can only be applied on a laboratory scale as it requires a specialized apparatus and is very time-consuming. At best only a few hundred milligrams of lipoproteins or apolipoproteins can be produced using this method over a course of a few days. Other methods of isolating apolipoproteins or lipoproteins have also been known for some time; they are based in many cases on precipitation by means of divalent cations and/or polyethylene glycol or dextran, for example. A further possibility of isolating apolipoproteins is precipitation by means of alcohol fractionation, as described in patent EP 0 329 605 B1. Using this lasts mentioned method it is possible to isolate larger quantities of apolipoprotein A-I (apoA-I) or fractions which are enriched in apoA-I, and to make them available for therapeutic applications. Using thus isolated apoA-I or protein fractions enriched in apoA-I, a series of experiments have been carried out, both with animals and with humans. Based on these experiments, both the safety of these products with respect to viruses could be shown and also that apoA-I in the form used leads to no significant side reactions in humans or animals. Nevertheless, in in vitro tests none of the desired activities could be found such as, for example, cholesterol transport or effects of apoA-I on cells such as neutrophils, macrophages, monocytes or platelets. In in vivo tests both in animals and in humans very short half-lives of apoA-I in plasma were observed. Because of the molecular weight of free apoA-I (28 000 Dalton), there exists the possibility that apoA-I is eliminated by the kidneys. apoA-I could in fact be detected in the urine of rabbits. These results demonstrate that apoA-I infused in large quantities is not distributed to the desired lipoprotein fraction. Due to its short half-life, apoA-I is able to have its effect in vivo at most for a very short time. Consequently a more suitable form of administration is achieved by infusing apoA-I in a lipoprotein or a lipoprotein-like particle.

Methods of producing reconstituted lipoproteins have been described in scientific literature, especially for apolipoproteins A-I, A-II, A-IV, apoC and apoE (A. Jonas, *Methods in Enzymology* 128, 553–582 (1986)). The is most frequent lipid used for reconstitution is phosphatidyl choline, extracted either from eggs or soybeans. Other phospholipids are also used, also lipids such as triglycerides or cholesterol. For reconstitution the lipids are first dissolved in an organic solvent, which is subsequently evaporated under nitrogen. In this method the lipid is bound in a thin film to a glass wall. Afterwards the apolipoprotein and a detergent, normally sodium cholate, are added and mixed. The added sodium cholate causes a dispersion of the lipid. After a suitable incubation period, the mixture is dialyzed against large quantities of buffer for a longer period of time; the sodium cholate is thereby removed for the most part, and at the same time lipids and apolipoproteins spontaneously form themselves into lipoproteins or so-called reconstituted lipoproteins. As alternatives to dialysis, hydrophobic adsorbents are available which can adsorb detergents (Bio-Beads SM-2, Bio Rad; Amberlite XAD-2, Rohm & Haas) (E. A. Bonomo, J. B. Swaney, *J. Lipid Res.*, 29, 380–384 (1988)), or the detergent can be removed by means of gel chromatography (Sephadex G-25, Pharmacia). Lipoproteins can also be produced without detergents, for example through incubation of an aqueous suspension of a suitable lipid with apolipoproteins, the addition of lipid which was dissolved in an organic solvent, to apolipoproteins, with or without additional heating of this mixture, or through treatment of an apoA-I-lipid-mixture with ultrasound. With these methods, starting, for example, with apoA-I and phosphatidyl choline, disk-shaped particles can be obtained which correspond to lipoproteins in their nascent state. Normally, following the incubation, unbound apolipoprotein and free lipid are separated by means of centrifugation or gel chromatography in order to isolate the homogeneous, reconstituted lipoprotein particles.

Described in U.S. Pat. No. 5,128,318 is a method of producing reconstituted HDL wherein phosphatidyl choline is dissolved in a solution with the aid of an organic solvent.

The methods for producing reconstituted lipoproteins described above are only suitable for smaller quantities of some milligrams to at most some grams on the laboratory scale:

- high dilutions of solutions in intermediate products make processing of the mixtures in the required time impossible;
- the necessary infrastructure for large volumes is normally not available;
- the organic solvents used are not environmentally acceptable;
- the final products cannot be stored;
- the concentration of the final product is too low, thus the volumes to be infused in the patient would be too large;
- the products normally have to be purified further, for example by means of gel chromatography to separate residual free lipid and/or free protein from the desired rHDL particles.

Furthermore described in A. Hubsch et al., *Circulatory Shock* 40, 14–23 (1993) is a method of producing reconstituted lipoproteins, wherein a ratio of apolipoprotein to lipid of 1:200 is used. The result of this procedure is that the product obtained has a considerable portion of free lipid, which unfavorably influences its therapeutic applicability.

For the therapeutic or prophylactic use of rHDL in humans, a dose of rHDL in gram quantities is necessary to achieve significant increases of the apoA-I or HDL level in the plasma. Thus, the economical production of rHDL for clinical purposes on a kilogram or larger scale is not possible with the methods described above.

SUMMARY OF THE INVENTION

Thus the object of this invention is to provide a method of producing rHDL which does not have the aforementioned drawbacks and whose product in particular has no large portions of free lipid or free apoA-I. A further object of the invention is to provide a method which can be carried out without the addition of organic solvents. It has been found that reconstituted lipoproteins, especially reconstituted HDL (rHDL), can be produced from apolipoproteins and lipids using simple, fast and industrially applicable means.

The subject matter of this invention is therefore a method of industrially producing from apolipoproteins and lipids a preparation which contains reconstituted lipoprotein particles, and which, with a protein content of 20±2 g/l and at a temperature of 20° C.±2° C., has a turbidity of less than 40 NTU (nephelometric turbidity unit), wherein an aqueous apolipoprotein solution with a concentration of 1–40 g protein/l is mixed with an aqueous lipid-detergent solution without the addition of organic solvents, the molar ratio of lipid to detergent being in the range of 1:0.5 to 1:4.0 and the weight ratio of apolipoprotein to lipid being in the range of 1:1.5 to 1:5.0, the obtained apolipoprotein-lipid-detergent mixture being subsequently incubated at a temperature in the range of the phase change temperature of the lipid in water ±10° C., the detergent being separated by means of exclusion by size or adsorption on an adsorbent to the point where protein-lipid particles form with a diameter of 5–50 nm and a mass of 50 000 to 1 000 000 Dalton, in which, without further purification steps, more than 95% of the proteins used and more than 90% of the total lipids are bound.

The subject matter of this invention is also a method for industrially producing a stable lyophilisate containing reconstituted lipoprotein particles from apolipoproteins and lipids wherein an aqueous apolipoprotein solution with a concentration of 1–40 g protein/l is mixed with an aqueous lipid-detergent solution without mandatory addition of organic solvents, the molar ratio of lipid to detergent being in the range of 1:0.5 to 1:4.0 and the weight ratio apolipoprotein to lipid in the range of 1:1.5 to 1:5.0, the resultant apolipoprotein-lipid-detergent mixture being subsequently incubated at a temperature in the range of the phase transition temperature of the lipid in water ±10° C., the detergent being separated by exclusion by size or adsorption on an adsorbent to the point where protein-lipid particles form with a diameter of 5–50 nm and a mass of 50 000 to 1 000 000 Dalton, in which, without further purification steps, more than 95% of the protein used and more than 90% of the total lipid are bound, a fluid product being obtained which, with a protein content of 20±2 g/l and at a temperature of 20° C.±2° C., has a turbidity of less than 40 NTU, and the obtained product being stabilized through lyophilization using a stabilizer selected from the group of carbohydrates, such as e.g. sucrose or mannitol.

The apolipoproteins used are, for example, recombinant apolipoproteins, apolipoproteins from a concentrated fraction of apolipoprotein A-I from human plasma, fragments of apolipoproteins or natural, synthetic or recombinant polypeptides with amphipathic properties. The fragments of apolipoproteins can be obtained through chemical or enzymatic fragmentation of natural or synthetic apolipoproteins. As an example for chemical fragmentation, treatment with cyanogen bromide is mentioned, or for enzymatic cleavage a protease, such as e.g. trypsin.

The lipid-detergent solution used according to the invention contains as the lipid, for example, phospholipid which can originate from soybeans or from eggs, cholesterol, cholesterol-ester, fatty acids or triglycerides. The detergents are preferably bile acids or salts therefrom, for example, cholic acid-sodium salt or sodium-deoxycholic acid.

BRIEF DESCRIPTION OF THE DRAWING

The Figure shows elution profiles of size exclusion chromatography of rHDL samples, prepared using different ratios of apolipoprotein A-I to phosphatidyl choline. The elution curves of four different preparations are dipicted: (1) apoA-I; (2) apoA-I:phosphatidyl choline (PC) in a mol:mol ratio of 1:100; (3) apoA-I:PC in a mol:mol ratio of 1:150 ratio; and (4) apoA-I:PC in a mol:mol ratio of 1:200.

DETAILED DESCRIPTION OF THE INVENTION

The temperature given in this specification of 20°±2° C. encompasses all values which fall into the range of 18° C. to 22° C. The protein content of 20±2 g/l encompasses all concentrations in the range of 18 g/l to 22 g/l. The indication "phase transition temperature±10° C." encompasses all temperatures which fall into the range between the temperature which is 10° C. lower than the phase transition temperature in an aqueous milieu of the corresponding lipid and the temperature which is 10° C. higher than the phase transition temperature of the lipid. The values cover a range between the freezing point of the solution and 50° C., where temperatures below 25° C. are preferred.

Preferred as starting material are lipoproteins purified from human plasma, which have been virus inactivated using suitable means, such as, for example, pasteurization. The denatured proteins (aggregates) which result through this procedure are subsequently renatured through incubation at a is weakly alkaline pH and slightly raised temperature in the presence of a chaotropic component, such as, for example, urea or guanidine-hydrochloride, so that after a buffer exchange of the protein in 10 mM NaCl>70% of the apoA-I is in monomeric form (determination by means of analytical size exclusion chromatography: 40 µg apoA-I was applied on a TSK G3000SW ULTROPAC column (LKB), in 10 mM sodium phosphate, 0.02% sodium azide, pH 7.4, with a flow of 0.4 ml/min; measurement of the eluate at 280 nm).

In further processing, lipoproteins in high concentration are mixed with a solution of lipids (phospholipids such as phosphatidyl choline, cholesterol, triglycides, etc.) in a solution of bile acids or their salts (e.g. cholate, deoxycholate, ursodeoxycholate) without organic solvents. In contrast to work described by Hubsch et al. (*Circulatory Shock* 40, 14–23 (1993)), the ratio of apolipoproteins to lipids is selected in such a way that neither large quantities of free lipids nor large quantities of free apolipoproteins are to be found in the final product, and so further purification of the rHDL can be omitted. In particular the ratio apoA-I: PC is reduced, the ratio being considerably below 1:200 (M:M; weight ratio approximately 1:5.5), namely to a ratio in the range of 1:50 to 1:180, preferably 1:100 to 1:150 (mol ratio; corresponding to a weight ratio of 1:2.8 to 1:4.2 for apoA-I and PC from soy). This, combined with a diafiltration method, leads to a drastic reduction of the content of free lipids (quantified by means of size exclusion chromatography; gel filtration by means of Superose 6; see below), and at the same time to a considerably lower concentration of bile acids in the final product; both high concentrations of bile acids and high content of free PC can lead to damage of cells in in vitro and in vivo, and therefore must be precisely controlled. The cholate concentration is optimized, on the one hand, to the ratio apoA-I: PC, and at the same time, if necessary, harmonized with further additions of lipid, especially cholesterol. Here, too, the optimal concentration is determined by as small a portion of free lipids and free apoA-I in the final product as possible; for an rHDL preparation with an apoA-I:PC ratio of 150, a molar ratio of Na-cholate is found of 1:200 (i.e. apoA-I:PC:Na-cholate= 1:150:200 (M:M:M) during the incubation to be now described). Following an incubation of 4–16 h at 0° C.–2° C. (for PC from soy) the concentration of the bile acids is reduced by means of diafiltration, with an ultrafiltration membrane having a pore size for globular proteins of between 1 000 and 100 000 Dalton, preferably below 30 000 Dalton. The buffer necessary therefore has a low ionic strength of below 100 mmol/l, preferably below 10 mmol/l, with a pH of above 6, preferably 7.5–9, and contains low concentrations of a carbohydrate, for example 1% sucrose. Under these conditions, 1 l to maximally 2 l of buffer per gram of protein used suffices to achieve, on the one hand, the necessary low detergent concentration, and, on the other hand, the desired distribution of particle size; these buffer volumes are many times smaller (10–200 times) than in methods previously described. If necessary, the detergent concentration is lowered to the desired concentration with an additional adsorption step with amberlite XAD-2. Using the aforementioned technology of diafiltration, the product is adjusted to a high concentration of 10–50 g protein/l, and subsequently processed in the presence of a stabilizer such as sucrose into a stable, storable end product (fluid or lyophilized). The lyophilisate is dissolved with water prior to use, producing a clear, slightly opalescent, solution which, depending upon lipid content, is light yellowish in color. In this solution the rHDL particles (disks) measured after processing could be detected again in practically unchanged form. By means of size exclusion chromatography, proportions of <10% aggregates (for the most part free lipid) and <5% free apolipoprotein were found. The turbidity in the fluid final product, determined before or after lyophilization, is under 40 NTU for a protein concentration of 20 g/l. The cholate content, measured with an enzymatic color test, is usually less than 0.5 g cholic acid—sodium salt per g protein (The detection of bile acids takes place through the formation of NADH in the presence of AND+ with the aid of 3-α-hydroxysteroid-dehydrogenase; the NADH formed reacts with nitrotetrazolium blue under catalysis of diaphorase forming a blue formazan derivative, which is detected photometrically).

Seen through an electron microscope after dissolution in a suitable volume of solvent, preferably water, the lyophilized rHDL are present as disk-shaped particles, analogous to nascent HDL, having a diameter of 5–50 nm normally 8–20 nm and a thickness of 2–6 nm. With analytical methods to determine particle sizes and their relative distribution, for example through gel filtration (size exclusion chromatography) in a physiological buffer with a SUPEROSE® 6 HR 10/30 column (Pharmacia Biotech), more than 80% of the particles are in the molecular weight range of 100 000 to 1 000 000 Dalton. Likewise more than 80% of the particles have a molecular weight distribution in the range of 50 000 to 1 000 000 Dalton, based on a gradient-gelelectrophoresis (method according to A. V. Nichols et al., Methods in *Enzymology* 128, 417–431 (1986)).

The single figure serves the better understanding of the invention and supports the aforementioned embodiments. It shows an elution diagram (absorption-elution diagram over time) of gel filtrations of rHDL particles, produced by using different ratios of apoA-I to phosphatidyl choline (apolipoprotein to lipid ratios). [High Performance Size Exclusion Chromatography of apoA-I and rHDL particles; separation of 200 μg rHDL in 100 μl 0.9% NaCl on a SUPEROSE® 6 HR 10/30 column (Pharmacia Biotech) in PBS (10 mM sodium phosphate, 150 mM NaCl, pH 7.4) with a flow of 0.5 ml/min.]. The absorption of the columnar eluate was measured at 280 nm (L. L. Rudel, C. A. Marzetta and F. L. Johnson, *Methods in Enzymology* 129, 45–57 (1986). To determine the content of individual fractions in the chromatogram, the area under the curve is calculated. With an elution curve of the 1:200 product, it can be seen that at the beginning of the elution free lipids are washed out while this is not the case with the 1:100–1:150 products. As a comparison, the curve of the pure apolipoprotein (apoA-I) has been likewise indicated.

The following examples explain the present invention further; they are not to be understood as a limitation of the definition of the invention, however.

EXAMPLE 1

One kg of apoA-I was dissolved in 500 l 0.15 mol/l NaCl. The lipid solution was produced separately as follows: phosphatidyl choline from soybean oil (PHOSPHOLIPON 90®, Nattermann, Cologne, Germany) was dissolved in a buffer consisting of 10 mmol/l TRIS/HCl, 150 mmol/l NaCl, 1 mmol/l EDTA, pH 8.0, 2.8 kg phosphatidyl choline and 2.325 kg cholic acid sodium salt were dissolved in this buffer to 100 l. It was stirred for 1–2 hours, and, if necessary, heated to about 40° C., until the solution was clear. It was subsequently cooled down to 4° C. and 100 l of this lipid-cholate-solution were mixed with 1 kg apoA-I in 500 l. The mixture was stirred slowly overnight at 2°–4° C., After this incubation it was filter sterilized and diafiltered at 4° C. with a Pellicon with PTGC cassettes, nominal molecular weight limit (NMWL)=10 000 Dalton: first with 4 volumes of 5 mmol/l sodium bicarbonate and subsequently 2 volumes of 10% sucrose, keeping the volume of the product at a constant level. The concentration was then raised slowly, until a protein concentration of 20 g/l was reached. The solution was again filter sterilized and filled into vials and subsequently lyophilized. During the whole procedure, care was taken that in particular the lipid solution was protected from air, light and too high a temperature. The final product, dissolved in a suitable quantity of water to obtain a protein concentration of 20±1 g/l, showed a molar ratio of apoA-I to phosphatidyl choline of 1:100 (mole:mole), less than 5% free lipid and a turbidity of less than 40 NTU.

EXAMPLE 2

Ten kg apoA-I were dissolved in 2000 l of 10 mmol/l NaCl. 1.38 kg cholesterol and 29.9 kg of cholic acid sodium salt were stirred in 200 l of a buffer containing 10 mmol/l TRIS-HCl, 150 mmol/l NaCl, 1 mmol/l EDTA, pH 8.0. The temperature was raised to 65° C., and the mixture was stirred for two hours until a clear solution was obtained. Then It was cooled down to 20° C., and 27.9 kg of phophatidyl choline were added. The solution was then cooled down to 4° C., and stirred again for two hours. This mixture was added to the protein solution, was mixed, and then filter sterilized. The filtrate was stirred slowly overnight (for at least 16 hours) at 4° C. Then, keeping a constant volume of the product, aliafiltration took place using 4 volumes of 50 mmol/l NaCl, 1 mmol/l EDTA, pH 7.5, for 2–4 hours, followed by another 2 volumes of 10% sucrose. The concentration of the solution was then increased to 20 g/l protein concentration. The solution was then filter sterilized, filled into glass vials and lyophilized. The vials were vacuum sealed and kept in the dark at 4° C. Using this method, rHDL was obtained in a molar ratio of 1:100:10 apoA-I:phosphatidyl choline:cholesterol.

EXAMPLE 3

Producing an rHDL with a ratio of 1:150 apoA-I to phosphatidyl choline: 3.08 kg of sodium cholate were dissolved in 25 l of a buffer, 10 mmol/l TRIS-HCl, 10 mmol/l NaCl, 1 mmol/l EDTA, pH 8.0. Therein a further 4.2 kg of phosphatidyl choline were dissolved for 2 hours at room temperature. Then 1 kg of apoA-I in 200 l 10 mmol/l NaCl was added, and the mixture incubated overnight at 0°–4° C. Then diafiltration was carried out at a constant volume against 4 volumes of 50 mmol/l NaCl, 1 mmol/l EDTA, pH 7,5, for 4 hours, and further against 2 volumes of 1% sucrose. Finally the concentration was increased to 20 g/l; of protein. The sucrose concentration was raised to 10% by addition of more solid sucrose. The solution was filter sterilized and lyophilized.

EXAMPLE 4

Producing an rHDL with a ratio of apoA-I to phosphatidyl choline to cholesterol of 1:100:10:4.61 kg of sodium cholate were dissolved in 25 l of a buffer comprising 10 mmol/l TRIS-HCl, 10 mmol/l NaCl, 1 mmol/l EDTA, pH 8.0. 138 g of cholesterol were dissolved at 65° C. in this buffer-cholate mixture for 2 hours. Then the mixture was cooled down to room temperature, and 2.8 kg of phosphatidyl choline dissolved therein for 1 hour. 1 kg apoA-I in 200 l 10 mmol/l NaCl was added. The mixture was incubated as in the previous example, likewise diafiltered, and the concentration increased as above.

EXAMPLE 5

ApoA-I to PC to cholesterol 1:150:10:5.38 kg of sodium cholate were dissolved in the buffer described in examples 3 and 4. 180 g of cholesterol were dissolved therein at 65° C. for 2 hours. Then 4.2 kg of PC were added and dissolved at room temperature for one hour. The mixture was added to 200 l of apoA-I solution, 5 g per liter in 10 mmol/l NaCl, and incubated overnight at 4° C. Diafiltration and production of the final product as above.

EXAMPLE 6

Producing an rHDL with low sodium cholate content. The rHDL were produced as in Examples 1–5. Following the diafiltration and the increasing of the concentration, one volume of rHDL solution was mixed with Amberlite XAD-2 (2 volumes) and this mixture was incubated with thorough mixing at 4° C. for one hour. Following incubation, the rHDL was removed by filtration, filter sterilized, and lyophilized as described in Examples 1–5.

EXAMPLE 7

400 g of apoA-I in 80 ml of 10 mmol/l NaCl were mixed with a lipid solution consisting of 1.66 kg of phosphatidyl choline, 1.23 kg of sodium cholate in a buffer described in examples 3–6. The mixture was incubated at 0°–2° C. for 16 hours. Then it underwent diafiltration using 4 volumes of EDTA (0.1 mmol/l) and then 2–4 volumes of sucrose (1%), and finally the concentration was increased to 21–25 g/l protein concentration. The rHDL solution was subsequently adjusted to a final concentration of 10% sucrose and 20 g/l of protein. It was filter sterilized and filled in portions of 50 g (1 g rHDL in 50 ml vials) and lyophilized.

EXAMPLE 8

From 980 kg of precipitate IV (Kistler, P., Nitschmann, H.; Vox Sang. 7, 414–424 (1962)), 11.2 kg of precipitate apoA-I were obtained through precipitation by alcohol. This was suspended in a three fold volume of 4-molar guanidine hydrochloride solution. The pH was adjusted to 5.2, and the solution pasteurized at 60° C. for 10 hours. The protein was solubilized at pH 7.5 and 45° C. After a filtration, a buffer exchange with a 10 mM NaCl solution took place by means of gel filtration on SEPHADEX G-25 (Pharmacia Biotech). 160 kg of apoA-I solution were obtained containing a total of 1040 g of apoA-I. The protein solution was incubated with a lipid solution for 2 to 16 hours at 0 to 2° C. The lipid solution was produced separately at room temperature: phosphatidyl choline from soybean oil was dissolved in a buffer described in examples 3–7. Dissolved in 26 kg of this buffer were 3203 g of sodium cholate and 4460 g of phosphatidyl choline. In the subsequent diafiltration (NMWL=10 000 Dalton), first the concentration of the protein-lipid mixture was raised to 7 g protein/l. Then diafiltration took place against a 1% sucrose solution until a cholate content of less than 4 g/l was achieved. The pH was always kept at at least 7.5. Finally the concentration of the solution was increased to 25 g/l of protein, and was stabilized with sucrose. The final product was adjusted to a protein concentration of 20 g apoA-I/l and 100 g sucrose/l, and was sterile filtered. In the size exclusion chromatography, less than 5% free lipid and less than 1% free apoA-I were found. The protein-lipid mixture was filled in portions of 50 ml each, and lyophilized. The final product dissolved in a suitable quantity of water showed a molar ratio of apoA-I:phosphatidyl choline of 1:140 [mol:mol].

We claim:

1. A method of industrially producing a preparation containing reconstituted high density lipoprotein (rHDL) particles from apolipoprotein A-I and phosphatidyl choline, having, at a protein content of 20±2 g/l and at a temperature of 20° C.±2° C., a turbidity of less than 40 NTU, comprising the stops of:

(a) making an apolipoprotein A-I-phosphatidyl choline-detergent mixture by mixing (1) an aqueous apolipoprotein A-I solution having a protein concentration of 1–40 g/l with (2) an aqueous phosphatidyl choline-detergent solution prepared without the use of organic solvents and having a molar ratio of phosphatidyl choline to detergent in the range of 1:0.5 to 1:4.0, whereby the ratio of the apolipoprotein A-I solution to the phosphatidyl choline-detergent solution is selected such that the weight ratio of apolipoprotein A-I to phosphatidyl choline ranges from 1:1.5 to 1:5.0;

(b) incubating the obtained apolipoprotein A-I-phosphatidyl choline-detergent mixture at a temperature of the phase change temperature equal to phosphatidyl choline in water±10° C.; and (c) removing the detergent by means of diafiltration to the point where apolipoprotein A-I-phosphatidyl choline particles form with a diameter of 5–50 nm and a mass of 50,000 to 1,000,000 Dalton;

whereby without further purification steps, a preparation of apolipoprotein A-I-phosphatidyl choline particles is obtained in which more than 95% of the apolipoprotein A-I used and more than 90% of the total phosphatidyl choline used are bound.

2. A method of industrially producing a preparation containing reconstituted high density lipoprotein (rHDL) particles from recombinant apolipoprotein A-I and phosphatidyl choline, having, at a protein content of 20±2 g/l and at a temperature of 20° C.±2° C., a turbidity of less than 40 NTU, comprising the steps (a) making an apolipoprotein A-I-phosphatidyl choline-detergent mixture by mixing (1) an aqueous solution of recombinant apolipoprotein A-I having a protein concentration of 1–40 g/l with (2) an aqueous phosphatidyl choline-detergent solution prepared without the use of organic solvents and having a molar ratio of phosphatidyl choline to detergent in the range of 1:0.5 to 1:4.0, whereby the ratio of the apolipoprotein A-I solution to the phosphatidyl choline is within the range of 1:1.5 to 1:5.0;

(b) incubating the obtained apolipoprotein A-I-phosphatidyl choline-detergent mixture at a temperature of the phase change temperature equal to phosphatidyl choline in water±10° C.; and (c) removing the detergent by means of diafiltration to the point where apolipoprotein A-I-phosphatidyl choline particles form with a diameter of 5–50 nm and a mass of 50,000 to 1,000,000 Dalton;

whereby, without further purification steps, a preparation of recombinant apolipoprotein A-I-phosphatidyl choline particles is obtained in which more than 95% of the recombinant apolipoprotein A-I used and more than 90% of the total phosphatidyl choline used are bound.

3. A method of industrially producing a preparation containing reconstituted high density lipoprotein (rHDL) particles from a fragment of apolipoprotein A-I or recombinant apolipoprotein A-I and phosphatidyl choline, having, at a protein content of 20±2 g/l and at a temperature of 20° C.±2° C., a turbidity of less than 40 NTU, comprising the steps of:

(a) making an apolipoprotein A-I-phosphatidyl choline-detergent mixture by mixing (1) an aqueous solution of a fragment of apolipoprotein A-I or recombinant apolipoprotein A-I having a protein concentration of 1–40 g/l with (2) an aqueous phosphatidyl choline-detergent solution prepared without the use of organic solvents and having a molar ratio of phosphatidyl choline to detergent in the range of 1:0.5 to 1:4.0, whereby the ratio of the solution of a fragment of apolipoprotein A-I or recombinant apolipoprotein A-I to the phosphatidyl choline-detergent solution is selected such that the weight ratio or apolipoprotein A-I to phosphatidyl choline is within the range of 1:1.5 to 1:5.0;

(b) incubating the obtained mixture of the fragment of apolipoprotein A-I or recombinant apolipoprotein A-I and detergent at a temperature equal to phase change temperature of the phosphatidyl choline in water±10° C.; and (c) removing the detergent by means of diafiltration to the point where particles of fragments of apolipoprotein A-I-phosphatidyl choline or recombinant apolipoprotein A-I-phosphatidyl choline form with a diameter of 5–50 nm and a mass of 50,000 to 1,000,000 Dalton;

whereby, without further purification steps, a preparation of particles of fragments of apolipoprotein A-I or recombinant apolipoprotein A-I and phosphatidyl choline is obtained, in which more than 95% of the fragments of apolipoprotein A-I or recombinant apolipoprotein A-I used and more than 90% of the total phosphatidyl choline used are bound.

4. A method for industrially producing a stable lyophilisate containing reconstituted high density lipoprotein (rHDL) particles from apolipoprotein A-I and phosphatidyl choline, comprising the steps of:

(a) making an apolipoprotein A-I-phosphatidyl choline-detergent mixture by mixing (1) an aqueous apolipoprotein A-I solution having a protein concentration of 1–40 g/l with (2) an aqueous phosphatidyl choline-detergent solution prepared without the use of organic solvents and having a molar ratio of phosphatidyl choline to detergent in the range of 1:0.5 to 1:4.0, whereby the ratio of the apolipoprotein A-I solution to the phosphatidyl choline-detergent solution is selected such that the weight ratio of apolipoprotein A-I to phosphatidyl choline is within the range of 1:1.5 to 1:5.0;

(b) incubating the obtained apolipoprotein A-I-lipid-detergent mixture at a temperature of the phase change temperature equal to phosphatidyl choline in water±10° C.;

(c) removing the detergent by means of diafiltration to the point where apolipoprotein A-I-phosphatidyl choline particles form with a diameter of 5–50 mn and a mass of 50,000 to 1,000,000 Dalton, in which more than 95% of the apolipoprotein A-I used and more than 90% of the total phosphatidyl choline are bound; and (d) stabilizing the obtained liquid product, at a protein content of 20±2 g/l and at a temperature of 20° C.±2° C., having a turbidity of less than 40 NTU, through lyophilization in the presence of a stabilizer selected from the group of carbohydrates.

5. The method according to any one of claims 1–4, wherein in step (c) at most 2 liters of buffer per gram of protein is used.

6. The method according to any one of claims 1–4, wherein the phosphatidyl choline-detergent solution further comprises other phospholipids, cholesterol, cholesterol esters, fatty acids or triglycerides.

7. The method of claim 1, wherein the aqueous apolipoprotein A-I solution is a fraction from human plasma enriched in apolipoprotein A-1 which has been treated with at least one virus inactivation step by means of incubation in a solution containing chaotropic components and subsequent change of buffer in a solution with an ionic strength of less than 50 mmol/l after which more than 70% of the lipoproteins are in monomeric form.

8. The method according to any one of claims 1–4, wherein the phosphatidyl choline-detergent solution further comprises other phospholipids.

9. The method according to any one of claims 1–4, wherein the phosphatidyl choline is synthetic phosphatidyl choline.

10. The method of claim 4, wherein the natural phosphatidyl choline is extracted from soybeans or eggs.

11. The method according to any one of claims 1–4, wherein the phospholipid is soy phosphatidyl choline, and the incubation of the apolipoprotein-lipid-detergent mixture takes place at a temperature of 0°–15° C.

12. The method according to any one of claims 1–4, wherein the detergent used is selected from the class of bile acids or a salt therefrom.

13. The method of claim 12, wherein the detergent is cholic acid sodium salt or sodium—deoxycholic acid.

14. The method according to any one of claims 1–4, wherein after incubation of the phosphatidyl choline-apolipoprotein-detergent mixture, the content of detergent is reduced by diafiltration to a concentration of less than 0.5 g detergent per g protein.

15. The method according to any one of claims 1–4, wherein before or after the separation of the detergent, the protein concentration is increased to 10–50 g/l by means of diafiltration.

16. The method according to any one of claims 1–4, wherein the aqueous apolipoprotein solution or the phosphatidyl choline-detergent solution is buffered at a pH in the range of pH 6 to pH 9.

17. The method of claim 16, wherein the aqueous apolipoprotein solution or the phosphatidyl choline-detergent-solution is buffered at a pH in the range of pH 7.5 to pH 8.5.

18. The method of claim 4, wherein the product is adjusted to a protein concentration of 5–50 g/l and the lyophilization of the solution to stabilize the product takes place in the presence of 5–15% of a disaccharide or 2–10% of a monosaccharide or 2–10% of mannitol.

19. The method of claim 18, wherein the disaccharide is sucrose.

20. The method according to claim 8, wherein the phosphatidyl choline is a natural phosphatidyl choline.

* * * * *